United States Patent [19]

McNamara et al.

[11] Patent Number: 5,770,588
[45] Date of Patent: Jun. 23, 1998

[54] NON-ANTIBACTERIAL TETRACYCLINE COMPOSITIONS OF THE PREVENTION AND TREATMENT OF ROOT CARIES

[75] Inventors: Thomas F. McNamara, Port Jefferson; Lorne M. Golub; Nangavarum S. Ramamurthy, both of Smithtown, all of N.Y.

[73] Assignee: The Research Foundation of State University of New York, Albany, N.Y.

[21] Appl. No.: 591,949

[22] Filed: Jan. 23, 1996

Related U.S. Application Data

[63] Continuation of Ser. No. 164,478, Dec. 9, 1993, abandoned, which is a continuation-in-part of Ser. No. 874,369, Apr. 27, 1992, abandoned, which is a continuation-in-part of Ser. No. 654,073, Feb. 11, 1991, Pat. No. 5,223,248.

[51] Int. Cl.$^6$ ................................................ A61K 31/65
[52] U.S. Cl. ........................................................ 514/152
[58] Field of Search ............................................ 514/152

[56] References Cited

U.S. PATENT DOCUMENTS

| | | |
|---|---|---|
| 3,275,513 | 9/1966 | Nash et al. . |
| 4,197,318 | 4/1980 | Sipos ........................................ 424/661 |
| 4,369,172 | 1/1983 | Schor et al. . |
| 4,411,889 | 10/1983 | Caslavsky et al. ...................... 424/601 |
| 4,454,110 | 6/1984 | Caslavsky et al. ........................ 424/54 |
| 4,563,351 | 1/1986 | Caslavsky et al. ........................ 424/52 |
| 4,666,897 | 5/1987 | Golub et al. . |
| 4,704,383 | 11/1987 | McNamara et al. . |
| 4,780,320 | 10/1988 | Baker ...................................... 514/152 |
| 4,892,736 | 1/1990 | Goodson ................................ 514/152 |
| 4,906,670 | 3/1990 | Higashi et al. . |
| 4,919,939 | 4/1990 | Baker ...................................... 514/152 |
| 4,925,833 | 5/1990 | Golub et al. . |
| 4,933,182 | 6/1990 | Higashi et al. .......................... 514/902 |
| 4,935,411 | 6/1990 | McNamara et al. . |
| 4,935,412 | 6/1990 | McNamara et al. . |
| 4,975,271 | 12/1990 | Dunn et al. ................................ 924/49 |
| 4,981,693 | 1/1991 | Higashi et al. .......................... 514/902 |
| 5,045,538 | 9/1991 | Schneider et al. . |
| 5,084,267 | 1/1992 | Damani .................................. 514/902 |
| 5,098,711 | 3/1992 | Hill et al. . |
| 5,223,248 | 6/1993 | McNamara et al. . |

OTHER PUBLICATIONS

"The Chemistry of the Tetracyclines", Chapter 6, 165–218 (1978) Marcel Dekker Publishers, Edited by Mitscher.
Newman et al., "Antibacterial Susceptibility of Plaque Bacteria", *J. Dent. Res.* 58 (7): 172–1732 (1979).
Golub et al., "In Vivo Crevicular Leukocyte Response to a Chemotactic Challenge: Inhibition by Experimental Diabetes", *Infection and Immunity* 37: 1013–1020 (1982).
Elewski et al., "In Vivo Suppression of Neutrophil Chemotaxis by Systemically and Topically Administered Tetracycline", *J. Amer. Acad. Dermatol.* 8: 807–812 (1983).

Deasy, et al., "Use of Strips Containing Tetracycline Hydrochloride or Metronidazole for the Treatment of Advanced Peridontal Disease", *J. Pharm. Pharmacol.*, 41, 694–699 (1989).
Sipo, et al., "The Effect of Collagenase Inhibitors on Alveolar Bone Loss Due to Periodontal Disease in Desalivated Rats", Matrix Metalloproteinase Conference, Abstract (1989).
Yu, et al., Serum Levels of Chemically–Modified Tetracycline (CMT) : A Comparison to Tetracycline (TC), *Journal of Dental Research*, Abstract (1990).
Golub, et al., "Low–dose Doxycycline Therapy: Effect on Gingival and Crevicular Fluid Collagenase Activity in Humans", *J. Periodont. Res.* 25:, 321–330 (1990).
Marcel Dekker, Publishers, N.Y., "Chemical Transformations Of The Tetracycline Family", *The Chemistry of Tetracyclines*, Chapter 6, (1978).
Newman, et al., "Antibacterial Susceptibility Of Plaque Bacteria", *J. Dent. Res.*, 58 (7): 1722–1732 (1979).
Golub, et al., "In Vivo Crevicular Leukocyte Response To A Chemotactic Challenge: Inhibition By Experimental Diabetes", *Infection and Immunity*, 37: 1013–1020 (1982).
Elewski, et al., "In Vivo Suppression Of Neutrophil Chemotaxis By Systemically And Topically Adminstered Tetracycline", *J. Am. Acad. Dermatol*, 8: 807–812 (1983).
Golub, et al., "Further Evidence That Tetracyclines Inhibit Collagenase Activity In Human Crevicular Fluid And From Other Mammalian Sources", *Journal of Periodontal Research*, 20: 12–23 (1985).
Yu, et al., "Serum Level Of Chemically–Modified Tetracycline (CMT) : A Comparison To Tetracycline (TC)", *Journal of Dental Research*, vol. 69: 245, Abstract 1092 (1990).
Golub, et al., "Tetracyclines (TCs) Inhibit Metalloproteinases (MMPs): In Vivo Effects In Arthritic And Diabetic Rats" and New In Vitro Studies, Abstract presented at Matrix Metalloproteinase Conference, Destin, Florida, Sep. 11–15, 1989.
Sipos, et al., "The Effects Of Collagenase Inhibitors On Alvelolar Bone Loss Due To Periodontal Disease In Desalivated Rats", Abstract Presented at Matrix Metalloproteinase Conference, Destin, Florida, Sep. 11–15, (1989).

*Primary Examiner*—Shep K. Rose
*Attorney, Agent, or Firm*—Hoffmann & Baron, LLP

[57] ABSTRACT

Methods of inhibiting root caries formation on mammalian tooth surfaces are disclosed. The methods include topically contacting the tooth root surfaces with an effective amount of a non-antibacterial tetracycline which is not systemically absorbed into the blood stream. In preferred embodiments, the tetracyclines are included in various oral hygiene products such as dentifrices, lozenges, chewing gums and the like to contact the tooth root surfaces.

9 Claims, No Drawings

NON-ANTIBACTERIAL TETRACYCLINE COMPOSITIONS OF THE PREVENTION AND TREATMENT OF ROOT CARIES

The present application is a continuation of Ser. No. 08/164,478 filed Dec. 9, 1993, now abandoned, which is a continuation-in-part of U.S. patent application Ser. No. 07/874,369 filed on Apr. 27, 1992 which is a continuation-in-part application of U.S. patent application Ser. No. 07/654,073, filed Feb. 11, 1991 which issued as U.S. Pat. No. 5,223,248 on Jun. 29, 1993.

BACKGROUND OF THE INVENTION

The present invention relates to methods of inhibiting root caries. In particular, the present invention relates to preventing root caries using non-antibacterial tetracyclines.

For several decades now, there has been an increased awareness of the relationship between plaque formation on tooth surfaces and dental cavities or caries. Dental plaque is generally regarded as a film of bacteria, bacterial polymers, salivary polymers, remnants of epithelial cells and leukocytes. The bacteria, principally *Streptococcus mutans*, use natural sugars such as sucrose and glucose, which are included in the diet as a nutrition source, and produce cement-like polymers which bind to the enamel of the tooth surface. Once bound, the bacteria cause demineralization of the enamel by secreting acids and ultimately causing enamel caries.

In the past, most efforts aimed at reducing plaque formation, dental caries and root caries have included reducing sugar intake, regular brushing, flossing and periodic removal of plaque by dental professionals.

In some cases, plaque formation on tooth surfaces may become excessive and even pathological leading to periodontal disease which causes both the gums and alveolar bone to recede, thereby exposing the roots. In these situations, it is often necessary to institute prophylactic measures. In the past, broad spectrum antibiotics such as tetracyclines and metronidazole have been used in the treatment of periodontal disease to reduce oral cavity microflora, which are the most virulent aspect of plaque and caries formation. Although antibiotic agents are effective in reducing the number and amount of bacteria responsible for plaque and caries formation, extended periods of antibiotic administration are avoided due to the high incidence of side effects. Side effects most often associated with long-term antibacterial agent usage include intestinal disturbances, overgrowth of opportunistic yeast and fungi, and most importantly, the development of antibiotic-resistant bacteria.

The roots of teeth are also susceptible to caries formation. Root caries are an important cause of tooth loss in adults. Root caries can be especially prevalent when, due to periodontal disease, both the gums and alveolar bone recede causing exposure of the roots.

The roots of teeth are different from many tissues in the body in that roots, especially the exposed portion of the root resulting from recession of gingiva and bone, are not supplied with blood vessels. Since these roots lack blood vessels, they are not supplied with blood plasma in the same manner that other tissues of the body are supplied with blood plasma. As a consequence, treating the roots of teeth by systemic routes of administration, including oral ingestion of antibiotic and non-antibiotic compounds, which rely on the blood plasma level of an active agent for efficacy are not believed to be effective.

Tetracyclines, as stated above, are broad spectrum antibiotics and are active against most oral cavity microflora. The tetracycline compound exhibits the following general structure:

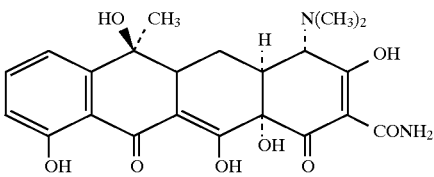

The numbering system of the ring nucleus is as follows:

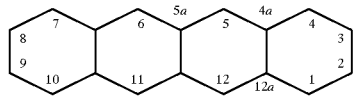

The tetracycline molecule is amenable to substantial modification without losing its antibiotic properties. Examples of modifications that may and may not be made to the basic tetracycline structure have been reviewed by Mitscher in the *Chemistry of Tetracyclines,* Chapter 6. According to Mitscher, the substituents at positions 5–9 of the tetracycline ring may be modified without complete loss of antibiotic properties. Changes to the basic ring system or replacement of the substituents at positions 1–4 and 10–12, however, generally lead to synthetic tetracyclines having substantially less or effectively no antibacterial activity. For example, 4-dedimethylaminotetracycline is commonly considered to be a non-antibacterial tetracycline.

Various properties of antimicrobial and non-antimicrobial tetracyclines are known. For example, it is known that antimicrobial and non-antimicrobial tetracyclines can bind to metal ions such as calcium. Tetracyclines are also known inhibitors of collagen destructive enzymes such as mammalian collagenase, a calcium dependent zinc-metalloproteinase.

U.S. Pat. No. 4,666,897 to Golub, et al. discloses tetracyclines, including commercially-available antimicrobial forms of the drug, systemically inhibit excessive bone resorption and collagenolytic enzyme activity when administered orally. U.S. Pat. No. 4,704,383 to McNamara, et al. discloses tetracyclines having substantially no effective antibacterial activity which systemically inhibit collagenolytic enzyme activity in rats when administered orally. Moreover, McNamara, et al. also disclose that non-antimicrobial tetracyclines reduce bone resorption in organ culture.

Copending U.S. Pat. No. 5,223,248 discloses a method of systemically inhibiting plaque formation and adhesion on mammalian tooth surfaces using non-antibacterial tetracyclines which are administered orally as a part of the mammal's daily meal.

Although some oral hygiene products such as dentifrices have been introduced to combat dental plaque, dental caries and root caries, a complete solution remains elusive. It was unexpected that the chemically-modified tetracyclines of the present invention (i.e., 4-hydroxy-4-dedimethylaminotetracycline and tetracylinonitrile) would be of any use since they are not systemically absorbed and therefore their useful activity was not fully recognized. These chemically-modified tetracyclines provide a further advantage in that the side effects associated with common systemic agents are avoided.

In view of the desire to reduce root caries and further in view of the desire to avoid using antimicrobial antibiotics to accomplish this result, it is an object of the present invention to provide an improved method of inhibiting the effect of caries on tooth root surfaces.

It is a further object of the present invention to provide a method of inhibiting caries formation on tooth root surfaces using systemically non-absorbed non-antibacterial tetracyclines.

SUMMARY OF THE INVENTION

In accordance with the present invention, it has been surprisingly found that systemically non-absorbable non-antibacterial tetracyclines when applied topically inhibit caries formation on tooth root surfaces in a manner completely separate from systemic antibacterial eradication of the oral cavity microflora. The method includes topically contacting the tooth root surfaces for a sufficient time with an effective amount of a non-antimicrobial tetracycline which results in the prevention of caries formation on tooth root surfaces. Generally, effective contact time varies from about 0.5 minutes to about 20 minutes and preferably from about 1 minute to about 5 minutes.

Up until now, it has generally been believed that non-antibacterial chemically-modified tetracyclines (CMTs) were absorbed systemically. Recently, it has been determined that certain chemically-modified tetracyclines (CMTs) are not absorbed when they are administered orally. When these CMTs are administered orally there is an absence of an increase in the level of CMT in the blood serum of recipients, indicating that these CMTs are either not absorbed or are poorly absorbed. Since these CMTs are not absorbed, they are known to be ineffective in the systemic inhibition of excessive bone resportion and collagenolytic enzyme activity. Non-absorption would also be expected to preclude other pharmacological activities generally attributed to oral administration of non-antibacterial CMTs. In any event, systemically absorbed CMTs would not be expected to be effective in the tooth root due to the lack of sufficient blood vessels to deliver these agents. However, these non-absorbed CMTs are effective at inhibiting root caries formation when applied topically.

The substantially systemically non-absorbable non-antimicrobial tetracyclines useful in the present invention are preferably chemically-modified tetracyclines (CMTs). Examples of such preferred tetracyclines include tetracyclinonitrile and 4-hydroxy-4-dedimethylaminotetracycline.

The amount of the non-antimicrobial tetracycline used in the methods of the present invention may be generally described as that amount which effectively inhibits caries formation on tooth root surfaces. For example, a non-antimicrobial tetracycline, may be included in dentifrices, mouthwashes or similar oral hygiene preparations in amounts ranging from about 10 mg % to about 100 mg %. In a preferred embodiment, the non-antimicrobial tetracycline is included in amounts of from about 10 mg % to about 25 mg %, with concentrations of about 20 mg % being most preferred. When contacting tooth root surfaces at these concentrations and for time periods typical for the oral hygiene product selected to contain the non-antimicrobial tetracycline, the non-antibacterial tetracyclines described herein prevent caries formation on tooth root surfaces. Naturally, the amount of the various tetracycline analogues will vary somewhat and the ranges set forth above are only illustrative of all possible dosage choices. Those skilled in the art will determine optimal concentrations for the desired non-antimicrobial tetracycline from clinical experience in order to carry out the present method.

As a result of the present invention, significant improvements in oral hygiene are realized. The present invention prevents caries effects on exposed root surfaces and on root surfaces below the gingival margin. Thus, the present invention inhibits steps in the pathological process of root decay. Moreover, the prophylaxis is achieved without using antimicrobial agents. Thus, the oral microflora remains intact. Antimicrobially-resistant strains of organisms, gastrointestinal disturbances and opportunistic yeast and fungi overgrowth which are associated with antimicrobial therapy are also beneficially avoided.

The present invention therefore offers a means of attacking root caries using agents which would otherwise be of little value if systemically absorbed. The effects of absorbable CMTs, which even if topically administered may find their way into the bloodstream can be avoided.

For a better understanding of the present invention, together with other and further objects, reference is made to the following description and its scope will be pointed out in the appended claims.

DETAILED DESCRIPTION OF THE INVENTION

In accordance with the present invention, methods for preventing root caries are disclosed. The method includes contacting tooth root surfaces for a sufficient time with an effective amount of a non-antimicrobial tetracycline which prevents root caries formation. Generally, effective contact time, i.e., the time sufficient for the systemically non-absorbable non-antibacterial tetracycline to interact with the root surface, varies from about 0.5 minutes to about 20 minutes and preferably from about 1 minute to about 5 minutes. These contact times may require repeated exposure on a regimented basis, e.g. daily, to provide adequate prophylactic protection. Consequently, they can be safely administered via topical delivery systems without fear of side effects due to systemic absorption.

The non-antimicrobial tetracyclines useful in carrying out the method of the present invention may be described as chemically modified tetracyclines (CMTs). For purposes of the present invention, CMT designates a tetracycline molecule which has been modified to essentially eliminate antimicrobial efficacy. Methods for altering and eliminating the antimicrobial efficacy of a tetracycline are disclosed in the *Chemistry of Tetracyclines,* Chapter 6, Mitscher, Ed., at page 211. As pointed out by Mitscher, modifications of the tetracycline molecule at positions 1, 2, 3, 4, 10 and 12a can lead to loss of antimicrobial activity.

Recently, it has been determined that certain chemically-modified tetracyclines (CMTs) are not absorbed when they are administered orally. When these CMTs are administered orally there is an absence of an increase in the level of CMT in the blood serum of recipients, indicating that these CMTs are either not absorbed or are poorly absorbed. Since these CMTs are not absorbed, they are known to be ineffective in the systemic inhibition of excessive bone resportion and collagenolytic enzyme activity. Non-absorption would also be expected to preclude other pharmacological activities generally attributed to oral administration of non-antibacterial CMTs. In any event, systemically absorbed CMTs would not be expected to be effective in the tooth root due to the lack of sufficient blood vessels to deliver these agents. However, these non-absorbed CMTs are effective at inhibiting root caries formation when applied topically.

Such chemically-modified tetracyclines (CMTs) which lack anti-bacterial activity and are not absorbed when administered orally include, for example, 4-hydroxy-4-dedimethylaminotetracycline and tetracyclinonitrile.

The amount of the tetracycline required to inhibit root caries is an amount which is effectively non-antimicrobial yet is effective in inhibiting root caries formation. The amount of non-antimicrobial tetracycline may also be described as a range. The highest amount is that amount which does not cause clinically detrimental side effects. For the purpose of the present invention, side effects would include any untoward reaction which would clinically warrant ceasing the tetracycline's administration. Such side effects of CMTs which are systemically absorbed include, for example, symptoms of toxicity. Of course, this is of no concern with the present invention because there is no systemic involvement, only topical. The lowest amount is that minimum amount which produces the desired anti-root caries result.

For illustrative purposes, non-antimicrobial tetracyclines can be included in vehicles such as dentifrices, mouthwashes, chewing gums, lozenges or other suitable dental hygiene preparations. In such embodiments, the tetracycline may be included in an amount of from about 10 mg % to about 100 mg %. In a preferred embodiment, the non-antimicrobial tetracycline may be present in amount of from about 10 mg % to about 25 mg %. In a most preferred embodiment, the non-antimicrobial tetracycline is present in an amount of about 20 mg %. The method of the present invention may then be carried out by using one of the dental hygiene products described above containing a non-antimicrobial tetracycline to contact the tooth root surfaces for a sufficient time to inhibit root caries.

As described above, the time required for the non-antimicrobial tetracycline to contact the tooth root surface and effectively inhibit root caries formation is conveniently the same amount of time as one is accustomed to for using oral hygiene products. For example, if the non-antimicrobial tetracycline is included in a toothpaste, normal brushing one to three times daily, for 1 to 5 minutes each time is sufficient. Similarly, contacting the teeth with an oral rinse containing the tetracycline for normal periods of around 1 to 5 minutes followed by expectorating one to three times daily would achieve the same result.

Tests were conducted using the method of the present invention to prevent caries formation on tooth root surfaces. The tests demonstrate the effectiveness and unexpected ability of non-antimicrobial tetracyclines which are not absorbed into the blood stream to prevent root caries on tooth root surfaces.

EXAMPLES

The following Examples serve to provide further appreciation of the invention, but are not, in any way, to be considered restrictive of the effective scope of the invention.

EXAMPLE I

The inability of tetracyclinonitrile (CMT-2) to be absorbed by an animal when administered orally was demonstrated using a group of six (6) adult Sprague-Dawley rats. The rats were each administered 5 mg/day of CMT-2 in 2% carboxymethyl cellulose (CMC) by oral gavage for twenty-one (21) days.

Blood was drawn at 24, 48 and 72 hour time points after the 21 day experimental protocol. The blood serum level of CMT-2 was assayed by HPLC (High Performance Liquid Chromatography). The serum concentration of CMT-2 was determined by comparison to a standard curve. The blood serum level of CMT-2 was assayed individually for each of the 6 rats. The blood serum concentrations ($\mu$g/ml) were averaged and are shown in Table 1.

Table 1 shows the blood serum concentration ($\mu$g/ml) of CMT-2 at 24, 48 and 72 hours after the 21 day experimental protocol.

TABLE 1

| | Serum Level ($\mu$g/ml) | | |
|---|---|---|---|
| | 24 hrs. | 48 hrs. | 72 hrs. |
| Tetracylinonitrile | 0.0 | 0.0 | 0.0 |

Table 1 shows that CMT-2 is not absorbed into the blood stream when administered orally. These results indicate that CMT-2 is ineffective systemically as a therapeutic agent. These results further indicate that any efficacious treatment using CMT-2 requires topical application of this chemically-modified tetracycline.

EXAMPLE II

The inability of tetracylinonitrile (CMT-2) to be absorbed by an animal when administered orally was verified using a group of six (6) adult Sprague-Dawley rats. The rats were each fed 5 mg/day of CMT-2 in 2% carboxymethyl cellulose (CMC) by oral gavage for twenty-one (21) days.

The rats were sacrificed and the liver, kidney and brain tissues were assayed for the presence of CMT-2. Extracts of the tissues were prepared in an appropriate solvent. The extracts were assayed by HPLC. The concentration of CMT-2 located in each tissue was determined by comparison to a standard curve. The concentration of CMT-2 in each tissue was assayed individually for each of the 6 rats. The tissue concentrations ($\mu$g/ml) of CMT-2 were averaged and are shown in Table 2.

Table 2 shows the concentration ($\mu$g/ml) of CMT-2 in liver, kidney and brain after the 21 day protocol.

TABLE 2

| | Concentration In Tissue ($\mu$g/ml) | | |
|---|---|---|---|
| | Liver | Kidney | Brain |
| Tetracyclinonitrile | 0.0 | 0.0 | 0.0 |

Table 2 shows that CMT-2 is not found in liver, kidney or brain when administered orally. These results verify that CMT-2 is not absorbed into the blood stream, since it is not cleared from the organism by either the liver or kidney.

These results further verify that CMT-2 is ineffective systemically as a therapeutic agent. In addition, these results show that efficacious treatment using CMT-2 requires topical application of this chemically-modified tetracycline.

EXAMPLE III

The inability of 4-hydroxy-4-dedimethylaminotetracycline (CMT-6) to be absorbed by an animal when administered orally was demonstrated using a group of six (6) adult Sprague-Dawley rats. The rats were each fed 5 mg/day of CMT-6 in 2% carboxymethyl cellulose (CMC) by oral gavage for twenty-one days.

Blood was drawn at 1, 2, 4, 8 and 24 hour time points after the 21 day experimental protocol. The blood serum level of CMT-6 was assayed by HPLC. The serum concentration of CMT-6 was determined by comparison to a standard curve. As previously described, the blood serum level of CMT-6 was assayed individually for each of the 6 rats. The blood serum concentrations ($\mu$g/ml) were averaged.

CMT-6 was not observed at any of the time periods mentioned above. Therefore, this experiment demonstrates that CMT-6 is not absorbed into the blood stream when administered orally. These results indicate that CMT-6 is ineffective systemically as a therapeutic agent. These results further indicate that efficacious treatment using CMT-6 requires topical application of this chemically-modified tetracycline.

EXAMPLE IV

The amelioration of root caries in *Porphymonas gingivalis* infected rats by 4-hydroxy-4-dedimethylaminotetracycline (CMT-6) was demonstrated using a group of twelve (12) male Sprague-Dawely rats. The gingival bacterial load of twelve normal barrier raised male Sprague-Dawely rats was reduced by daily administration of 20 mg of each of kanamycin and ampicillin. After seven days of drug therapy inside vinyl isolators, eight (8) rats were infected with black pigmented *Porghymonas gingivalis* grown to confluence on a chocolate agar plate containing vitamin K. Two (2.0) ml of sterile carboxymethyl cellulose (CMC) was pipetted directly onto the agar and the bacterial colonies were mixed with the CMC with a sterile cotton swab. The bacterial emulsion was then gently rubbed onto the gingival surface of each of the eight(8) rats, forcing the bacteria into the sulcus. This process was repeated daily for 4 days. During this time and throughout the experimental period rats were fed sterile food and water.

After infecting the rats for 4 days with *P. gingivalis*, the rats were left alone for an additional 7 days without any treatment. Control rats were swabbed with 2% CMC alone. Care was taken not to cross contaminate the rats.

The rats were then fed by oral gavage and exposed to the drug topically for 42 days as follows. Group I uninfected rats were administered 2% CMC/day (4 rats). Group II *P. gingivalis* infected rats were administered 0.5 cc of 2% CMC/day (6 rats). Group III *P. gingivalis* infected rats treated with CMT-6 were administered 5 mg CMT-6 in 0.5 cc of 2% CMC/day (2 rats). After 42 days of drug administration, the experiment was terminated by exsanguination of the rats. Maxillary and mandibular jaws were collected. One half was fixed in 10% buffered formalin and other half was defleshed for morphometric analysis.

Table 3 shows the number of root caries in each experimental group. The jaws were visually scored, in a blinded fashion, by two independent experienced examiners, to assess the severity of root caries formation in the three different groups of rats. The presence of root caries was very obvious when viewed under a dissecting microscope in *P. gingivalis* infected rats.

TABLE 3

Presence of Root Caries in *P. gingivalis* Infected Rats

|  | # of Root Caries |
|---|---|
| Group I |  |
| Control (4 rats) | 0 |
| Group II |  |
| *P. gingivalis* infected (6 rats) | 10 |
| Group III |  |
| *P. gingivalis* infected treated with CMT-6 (2 rats) | 0 |

The results in Table 3 clearly demonstrate that 4-hydroxy-4-dedimethylaminotetracycline (CMT-6) inhibits the formation of root caries. Since until now CMT-6 was not known to be non-absorbed, its usefulness as a pharmalogical agent was also not known. The administration of CMT-6 orally in 2% carboxymethyl cellulose results in topical contact of CMT-6 with the tooth root surfaces.

EXAMPLES V–IX

In these Examples, various oral hygiene products containing non-antimicrobial tetracyclines are set forth. These oral hygiene products are particularly suitable for use in humans, to which the claimed invention preferably applies. In each of the products, the term "CMT" is used to designate a chemically modified tetracycline such as a 4-hydroxy-4-dedimethylaminotetracycline and tetracyclinonitrile which essentially lack antimicrobial activity and are not absorbed when administered orally. Each of the following illustrative products is useful in providing a vehicle for allowing an effective amount of the tetracycline to contact the tooth root surface for a sufficient time and thereby inhibit root caries formation.

EXAMPLE V

Tooth Powder

| Ingredient | wt % |
|---|---|
| Silica hydrogel | 96.10 |
| Zinc chloride | 0.50 |
| Sodium fluoride | 0.22 |
| Sodium gluconate | 0.27 |
| Synthetic sweetener (saccharin/aspartame) | 0.50 |
| Sodium methyl cocoyltaurate | 1.50 |
| Flavoring | 0.80 |
| CMT | 0.01–0.10 |

EXAMPLE VI

Lozenge

| Ingredient | wt % |
|---|---|
| Sorbitol powder | 74.50 |
| Corn syrup | 15.00 |
| Zinc chloride | 0.50 |
| Sodium fluoride | 0.22 |
| Flavor and color | 1.15 |
| Sodium gluconate | 0.30 |
| Synthetic sweeteners | 0.20 |
| Tableting lubricant | 5.00 |
| Deionized water | 3.00 |
| CMT | 0.01–0.10 |

EXAMPLE VII

Chewing Gum

| Ingredient | wt % |
|---|---|
| Gum base | 30.00 |
| Sorbitol | 48.85 |
| Corn syrup | 15.00 |
| Flavor | 1.50 |
| Zinc chloride | 0.50 |
| Sodium fluoride | 0.22 |
| Sodium gluconate | 0.30 |
| Gum tragacanth | 0.50 |

-continued

| Ingredient | wt % |
| --- | --- |
| Deionized water | 3.00 |
| CMT | 0.01–0.10 |

EXAMPLE VIII

Dentifrice Composition

| Ingredient | wt % |
| --- | --- |
| Glycerin | 25.00 |
| Zeo 49B (Silicone Dioxide) | 21.50 |
| HMP (Hexaphos) | 6.00 |
| Syloid 244 (synthetic silica) | 3.00 |
| Sodium Lauryl Sulfate | 1.20 |
| Flavor | 1.00 |
| Sodium Hydroxide (50% Solution) | 1.00 |
| Xanthan Gum | 1.00 |
| Sodium Benzoate | 0.50 |
| Titanium Dioxide | 0.50 |
| Sodium Saccharin | 0.30 |
| Sodium Fluoride | 0.22 |
| CMT | 0.01–0.10 |
| Deionized water to Q.S. | 100 |

EXAMPLE IX

Mouthwash

| Ingredient | wt % |
| --- | --- |
| Ethyl Alcohol | 15.0 |
| Glycerol | 10.0 |
| Flavor | 0.4 |
| Sodium saccharin | 0.03 |
| Sodium Fluoride | 0.05 |
| Pluronic F 108 | 2.0 |
| CMT | 0.01–0.10 |
| Deionized Water to Q.S. | 100 |

Other formulations for self-treatment as well as professional treatment can be provided by skilled artisans. The present invention provides highly effective and reliable anti-root caries agents and treatments which can be used without the side effects associated with antibacterial tetracyclines.

While there have been described what are presently believed to be the preferred embodiments of the present invention, those skilled in the art will realize that changes and modifications may be made thereto without departing from the spirit of the invention, and it is intended to claim all such changes and modifications as fall within the true scope of the invention.

What is claimed is:

1. A method of treating tooth surfaces to prevent root caries in humans, comprising contacting topically said tooth root surfaces that are exposed as a result of recession of gingiva and alveolar bone due to periodontal disease for a sufficient time and with an effective amount sufficient to prevent root caries of a systemically non-absorbable non-antimicrobial tetracycline selected from the group consisting of 4-hydroxy-4-dedimethylaminotetracycline and tetracycilinonitrile.

2. A method of treating tooth surfaces to prevent root caries in mammals, comprising contacting topically said tooth root surfaces that are exposed as a result of recession of gingiva and alveolar bone due to periodontal disease for a sufficient time and with an effective amount sufficient to prevent root caries of a systemically non-absorbable non-antimicrobial tetracycline selected from the group consisting of 4-hydroxy-4-dedimethylaminotetracycline and tetracyclinonitrile.

3. The method of claim 1, wherein said non-antimicrobial tetracycline is present in an amount of from about 10 mg % to about 100 mg % by weight.

4. The method of claim 3, wherein said non-antimicrobial tetracycline is present in an amount of from about 10 mg % to about 25 mg %.

5. The method of claim 4, wherein said non-antimicrobial tetracycline is present in an amount of about 20 mg %.

6. The method of claim 1, wherein said non-antimicrobial tetracycline is incorporated into a dentifrice.

7. The method of claim 1, wherein said non-antimicrobial tetracycline is incorporated into a lozenge.

8. The method of claim 1, wherein said non-antimicrobial tetracycline is incorporated into a chewing gum.

9. The method of claim 1, wherein the non-antimicrobial tetracycline is contained in a mouthwash or an oral rinse product.

* * * * *

UNITED STATES PATENT AND TRADEMARK OFFICE
CERTIFICATE OF CORRECTION

PATENT NO. : 5,770,588
DATED : June 23, 1998
INVENTOR(S) : Thomas F. McNamara, et. al.

It is certified that error appears in the above-indentified patent and that said Letters Patent is hereby corrected as shown below:

Title page, item [54] and col. 1, line 2, title should read –Non- Antibacterial Tetracycline Compositions for the Prevention and Treatment of Root Caries--.

Drawings:

Add the Drawing sheets consisting of Figs. 1, 2, 3, 4, 5, 6, & 7 as showing on the attached pages.

Signed and Sealed this

Second Day of November, 1999

Attest:

Q. TODD DICKINSON

Attesting Officer

Acting Commissioner of Patents and Trademarks

UNITED STATES PATENT AND TRADEMARK OFFICE
CERTIFICATE OF CORRECTION

PATENT : 5,770,588

DATED : June 23, 1998

INVENTOR(S) : Thomas F. McNamara, et al

Page 1 of 3

It is certified that error appears in the above-identified patent and that said Letters Patent is hereby corrected as shown below:

In column 4, after line 17, insert the following:

-- BRIEF DESCRIPTION OF THE DRAWINGS

Figure 1 shows a normal root surface without any caries at A, and containing vital pulp at B.

Figure 2 shows a normal root surface without any carie lesions at A, and vital pulp at B.

Figure 3 shows carious lesions on the root surface with bacterial plaque accumulation at A, and devitalized necrotic pulp at B.

Figure 4 shows a broken root surface with bacterial plaque accumulation at A, and necrotic infected pulp at B.

UNITED STATES PATENT AND TRADEMARK OFFICE
CERTIFICATE OF CORRECTION

PATENT : 5,770,588

DATED : June 23, 1998

INVENTOR(S) : Thomas F. McNamara, et al

Figure 1:
Figure 1 is a lateral view of root histology of molar teeth in the bony socket of control rat molars.
Figure 2:
Figure 2 is a cross-sectional view of root histology of molar teeth in the bony socket of control rat molars.
Figure 3:
Figure 3 is a lateral view of root histology of molar teeth in the bony socket of Porphymonas gingivalis infected rat molars.
Figure 4:
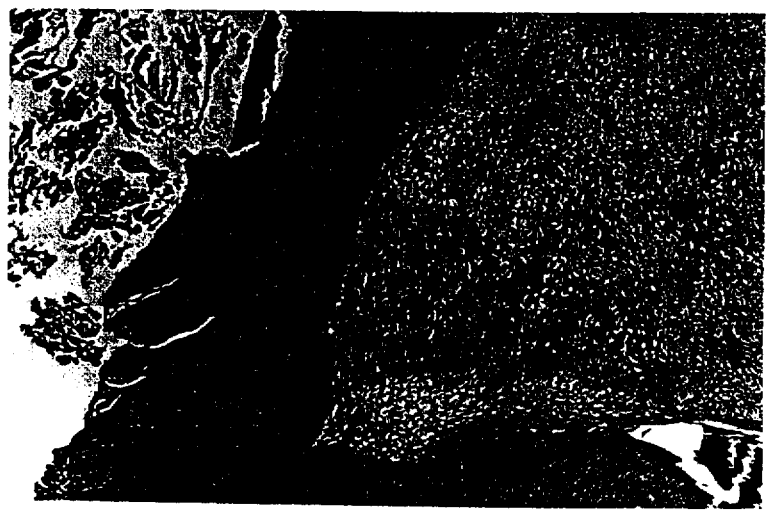
Figure 4 is a lateral view of root histology of molar teeth in the bony socket of P. gingivalis infected rat molars.
Figure 5:
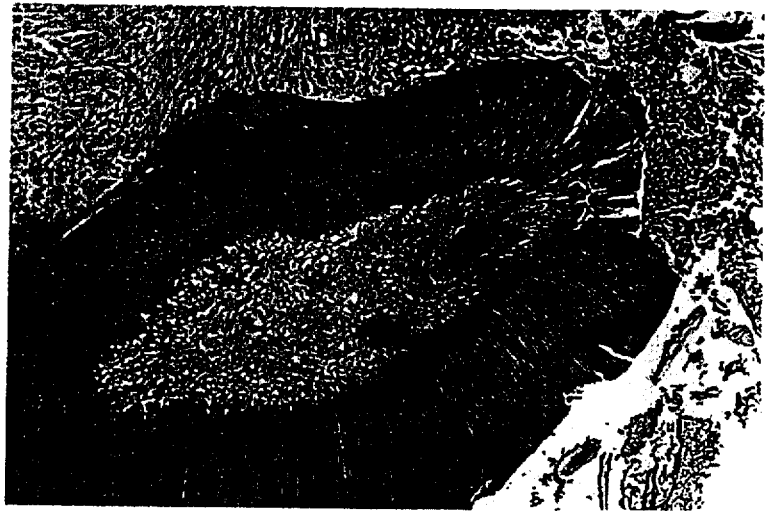

It is certified that error appears in the above-identified patent and that said Letters Patent is hereby corrected as shown below:

Figure 5 is a cross-sectional view of root histology of molar teeth in the bony socket of P. gingivalis infected rat molars. Figure 5 shows a broken root surface with bacterial plaque accumulation at A and infected devitalized pulp at B.

Figure 6:
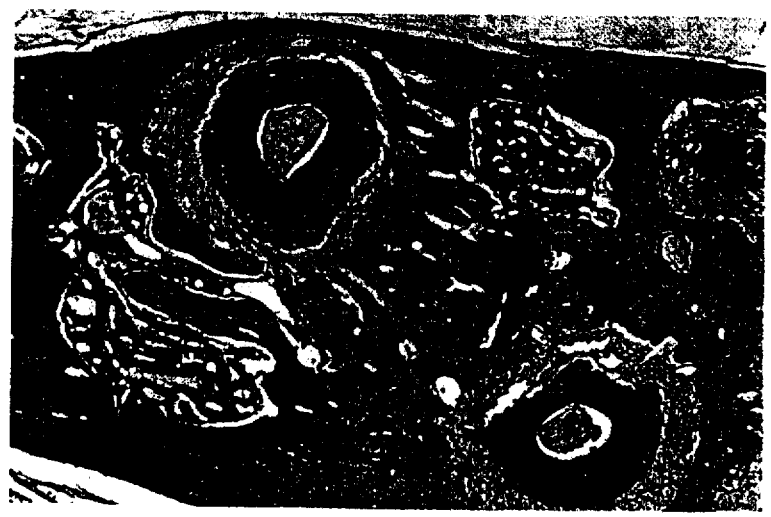

Figure 6 is a cross-sectional view of root histology of molar teeth in the bony socket of P. gingivalis infected rat molars which were treated with 5 mg of CMT-6 for 42 days. Figure 6 shows the normal root surface at A, and a vital pulp at B. Figure 6 evidences that topical applications of 5 mg of CMT-6 protected this rat from root caries formation.

Figure 7:

Figure 7 is a cross-sectional view of root histology of molar teeth in the bony socket of P. gingivalis infected rat molars which were treated with 5 mg of CMT-6 for 42 days. Figure 7 shows a normal root surface at A, and vital pulp at B. Figure 7 evidences that topical application of 5 mg of CMT-6 protected the rat from root caries formation.

UNITED STATES PATENT AND TRADEMARK OFFICE
CERTIFICATE OF CORRECTION

PATENT : 5,770,588

DATED : June 23, 1998

INVENTOR(S) : Thomas F. McNamara, et al

Figure 8:
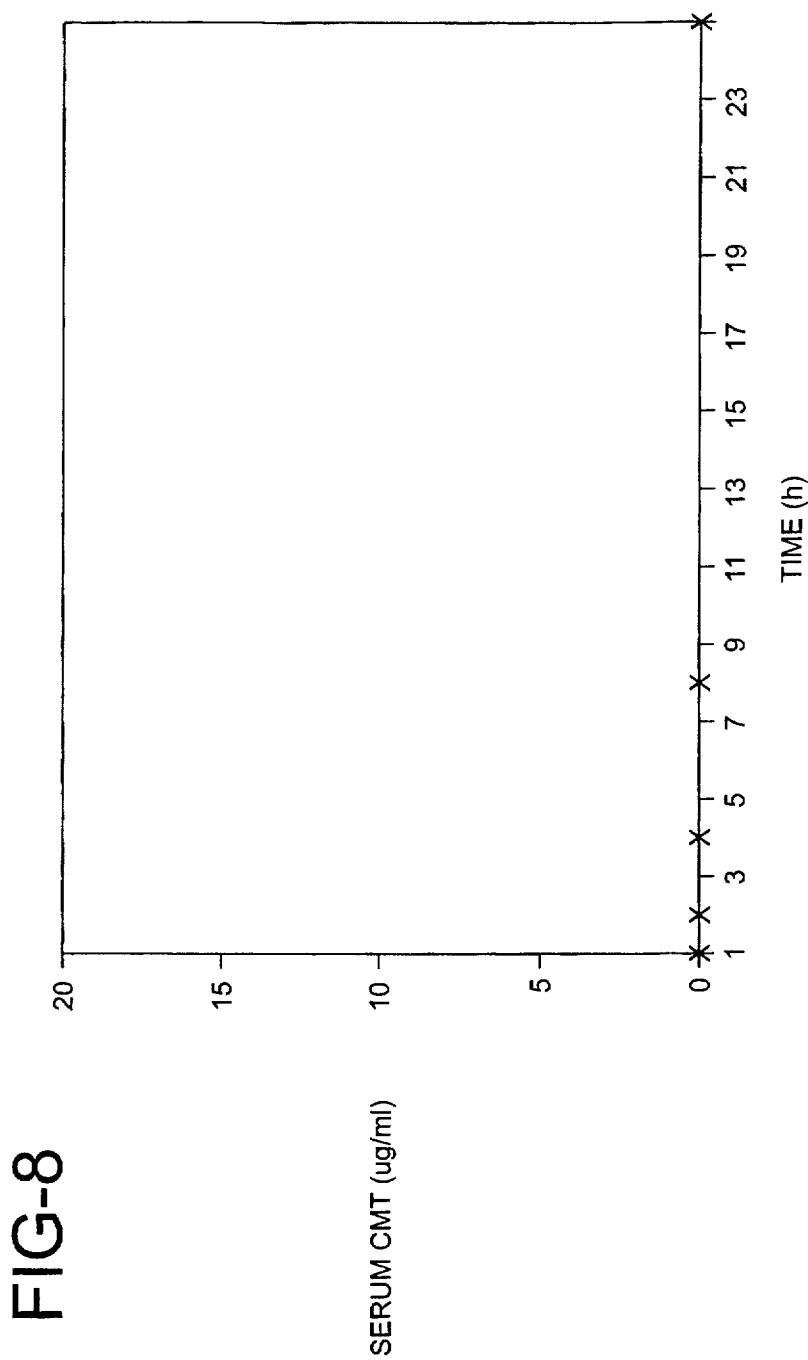

It is certified that error appears in the above-identified patent and that said Letters Patent is hereby corrected as shown below:

Figure 8 is a graphical representation of the serum concentration (µg/ml) of CMT-6 over time (hours). CMT-6 was administered by oral gavage at a dosage of 5 mg/day in 2% carboxymethyl cellulose (CMC) for 21 days prior to assay.

Signed and Sealed this

Fourth Day of April, 2000

Attest:

Q. TODD DICKINSON

Attesting Officer

Director of Patents and Trademarks